US008653457B2

(12) United States Patent
Stoks (10) Patent No.: US 8,653,457 B2
(45) Date of Patent: Feb. 18, 2014

(54) SPECTROSCOPY TECHNIQUE USING MERGED SPECTRAL DATA (71) Applicant: FEI Company, Hillsboro, OR (US)

(72) Inventor: Sander Richard Marie Stoks, Nijmegen (NL)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 13/946,755

(22) Filed: Jul. 19, 2013

(65) Prior Publication Data

US 2014/0021346 A1 Jan. 23, 2014

Related U.S. Application Data (60) Provisional application No. 61/674,549, filed on Jul. 23, 2012.

(30) Foreign Application Priority Data

Jul. 23, 2012 (EP) .................................... 12177454
Jul. 16, 2013 (EP) .................................... 13176233

(51) Int. Cl.
G01N 23/00 (2006.01)
G21K 7/00 (2006.01)
(52) U.S. Cl.
USPC ........... 250/307; 250/306; 250/310; 250/311; 378/44; 378/45; 378/46; 378/57
(58) Field of Classification Search
USPC ........ 250/306, 307, 310, 311; 378/44, 45, 46, 378/57
See application file for complete search history.

(56) References Cited

U.S. PATENT DOCUMENTS

| 6,519,315 | B2* | 2/2003 | Sommer et al. ................. 378/45 |
| 6,850,592 | B2* | 2/2005 | Schramm et al. ............... 378/45 |
| 7,366,282 | B2* | 4/2008 | Peschmann ..................... 378/57 |
| 7,899,153 | B2 | 3/2011 | Dugas et al. |
| 2004/0099805 | A1 | 5/2004 | Ochiai et al. |
| 2008/0205592 | A1 | 8/2008 | Conners et al. |

OTHER PUBLICATIONS

Galbreath, Kevin C., et al., "Feasibility of combined wavelenth/energy-dispersive computer-controlled scanning electron microscopy for determining trace metal distribution," Fuel Processing Technology, Aug. 1, 1994, pp. 63-72, vol. 39, No. 1-3.

(Continued)

Primary Examiner — Jack Berman
Assistant Examiner — Meenakshi Sahu
(74) Attorney, Agent, or Firm — Scheinberg & Associates, PC; Michael O. Scheinberg (57) ABSTRACT A method of examining a sample using a spectroscopic apparatus, comprising the following steps:
  Mounting the sample on a sample holder;
  Directing a focused input beam of radiation onto a location on the sample, thereby producing an interaction that causes a flux of stimulated photonic radiation to emanate from said location;
  Examining said flux using a multi-channel photon-counting detector, thus accruing a measured spectrum for said location;
  Automatically repeating said directing and examining steps for a series of successive locations on the sample,
which method comprises the following steps:
  Choosing a beam parameter of the input beam that will influence a magnitude of said flux of stimulated photonic radiation;
  For each location within a first set of locations on the sample, accruing a spectrum using a first value of said beam parameter;
  For each location within a second set of locations on the sample, accruing a spectrum using a second value of said beam parameter, different from said first value.

16 Claims, 3 Drawing Sheets (56) References Cited

OTHER PUBLICATIONS

Website 'http://en.wikipedia.org/wiki/Energy_Dispersive_Spectroscopy,' obtained Jul. 19, 2013, 3 pgs.

Website 'http://en.wikipedia.org/wiki/X-ray_fluorescence,' obtained Jul. 19, 2013, 8 pgs.

Website 'http://en.wikipedia.org/wiki/PIXE,' obtained Jul. 19, 2013, 3 pgs.

* cited by examiner

SPECTROSCOPY TECHNIQUE USING MERGED SPECTRAL DATA

The invention relates to a method of examining a sample using a spectroscopic apparatus, comprising the following steps:

Mounting the sample on a sample holder;

Directing a focused input beam of radiation onto a location on the sample, thereby producing an interaction that causes a flux of stimulated photonic radiation to emanate from said location;

Examining said flux using a multi-channel photon-counting detector, thus accruing a measured spectrum for said location;

Automatically repeating said directing and examining steps for a series of successive locations on the sample.

The invention also relates to a spectroscopic apparatus suitable for performing such a method, particularly as comprised in a charged-particle microscope.

For purposes of clarity and consistency, the following terms as used throughout this text and the appended claims should be interpreted as follows:

A focused beam is considered to be a beam having a confined cross-sectional area that is relatively small compared to the sample under investigation; in this way, it is possible to confine the beam's impingement footprint to relatively small sub-regions of the sample. The beam may be converging or collimated in nature.

Stimulated photonic radiation is considered to be photonic radiation that is produced as a result of atomic effects precipitated by bombardment with relatively high-energy particles (such as electrons, ions, X-rays or gamma rays). If the bombarding beam (input beam) is switched off, the flux of stimulated photonic radiation will cease. The term should not be confused with the concept of stimulated radiation as applied in laser science.

A multi-channel detector is considered to be a detector that can sort an incoming flux of photonic radiation into multiple energy channels, each representing a given energy range.

These points are elucidated in more detail below.

A method of the type described in the opening paragraph is known, for example, from the field of Energy-Dispersive X-ray Spectroscopy, which is often referred to using the acronyms EDX or EDS. In this technique, a sample (often, but not necessarily, mineralogical in nature) is bombarded with a focused input beam of charged particles (e.g. in a Scanning Electron Microscope, or in a dedicated standalone apparatus). A lower-shell electron in an atom of the sample can be ejected from its orbit by a collision with one of these bombarding particles, creating an electron hole that is promptly filled by the de-excitation of a higher-shell electron in the atom in question, with the concurrent release of a quantum of energy in the form of an X-ray photon. The energy signature/distribution of photons emitted in this way will be characteristic of the particular electron shell structure of the atom in question, and can thus be used as a "fingerprint" in performing elemental/compositional analysis of the sample. An energy-dispersive spectrometric detector collects, sorts and counts the different photons of different energies, producing a measured spectrum for the location of the sample onto which the focused input beam was directed; such a spectrum can be rendered as a graph of counts per channel (ordinate) versus channel number (abscissa), corresponding to intensity versus energy, and generally comprising various peaks—whose energy can be used to identify the generating element (substance) and whose height can (in principle) be used to estimate relative quantity of the generating element. One then automatically moves the sample and/or the beam so that the beam is directed onto a new location on the sample, and automatically repeats the process described above at said new location (such automatic actions being enacted, for example, with the aid of software that controls (aspects of) a processor/controller used to govern (aspects of) operation of the spectroscopic apparatus). This technique is particularly useful in the field of mineralogy, in which a small sample may contain many different kinds of minerals; however, its usefulness in fields such as metallurgy, microbiology and semiconductor science is also self-evident. For more information on EDX/EDS, reference is made to the following webpage:

http://en.wikipedia.org/wiki/Energy_Dispersive_Spectroscopy

As here employed, the term EDX/EDS encompasses so-called Wavelength Dispersive X-Ray Spectroscopy (WDX or WDS). This latter technique can be regarded as a particular refinement of EDX/EDS in which the X-rays emerging from a sample are filtered (e.g. with the aid of a particular type of crystal), so that only X-rays of a given wavelength are counted at any given time.

Another such known technique is X-Ray Fluorescence Spectroscopy, which is often referred to using the acronym XRF. This technique is similar to EDX/EDS, except that in the input beam comprises X-ray or gamma ray photons instead of charged particles. For more information on XRF, reference is made to the following webpage:

http://en.wikipedia.org/wiki/X-ray_fluorescence

Yet another such technique is Proton-Induced X-Ray Emission (PIXE), in which the input beam comprises protons. This technique is described in more detail in the following reference:

http://en.wikipedia.org/wiki/PIXE

Useful as they are, these known techniques do, however, suffer from certain setbacks. For example:

(i) One problem lies in the nature of the exploited physical process (ejection and de-excitation of bound electrons), and is caused by the fact that not all elements demonstrate the same "brightness" as regards the production of a photon via this mechanism. As a result, assuming a fixed counting time (accumulation time) during a measurement session, significantly different photon count numbers can be accrued for different elements in a sample. Even for a single element, an emission spectrum will typically comprise multiple peaks of different heights—some of which may be so high as to dominate the spectrum, while others may be little more than a slight bump in the obtained data. However, when simultaneously counting photons from several elements of significantly different brightnesses, the difference in magnitude between the highest and the lowest peaks can be even greater. Such a wide range of peak heights can cause smaller peaks to be missed/overlooked in background noise, unless the counting time is significantly increased; however, increasing the counting time in this manner necessarily incurs a significant throughput penalty, which is typically undesirable.

(ii) Another problem lies in the modus operandi of the employed detector, which sorts photons into different "channels" according to their perceived energy, and counts the number of photons in each channel within the allotted counting time. This sorting process is serial in nature, and can be thrown into confusion when the detector is confronted with the arrival of two consecutive photons in rapid temporal succession (an event conventionally referred to as a "pile-up"). Assuming these photons to have energies E1 and E2, respectively, the processing circuitry employed by the detector may be unsure as to whether it has just "seen" two distinct photons or a single photon of energy E1+E2, since the temporal separation of the photons is not sufficiently large to allow an inflection point between them to be confidently distinguished from noise effects. To avoid "spoiling" accrued data, such pile-up events are conventionally discarded by said processing circuitry. In measurement scenarios involving relatively high fluxes of stimulated photonic (X-ray) radiation from the sample, much potentially useful data may have to be discarded in this manner, so that measurement quality will inevitably suffer. It is somewhat ironic that, despite the high photonic flux, there may be relatively little useful data for the employed detector, as a result of which the obtained spectrum may be noisy and relatively low-resolution, and its peak height(s) can no longer be reliably used to estimate the relative quantity of the element(s) generating the peak(s) in question.

(iii) Problems (i) and (ii) tend to exacerbate one another. For example, consider an element having high brightness, as alluded to in (i). A high photonic flux produced by this element may "overwhelm" the processing circuitry of the employed detector, causing a drastic reduction in detection efficiency due to recurring pile-ups. This reduction, in turn, makes it even harder to effectively detect (weaker) spectral peaks due to elements with a lower brightness.

It is an object of the invention to address these issues. More specifically, it is an object of the invention to provide a spectroscopy method that can more effectively cope with the concurrent occurrence in a sample of elements having substantially discrepant brightnesses. Additionally, it is an object of the invention that such a method should be able to deal with data pile-ups in a more efficient manner.

These and other objects are achieved in a method as specified in the opening paragraph, characterized by the following steps:

Choosing a beam parameter of the input beam that will influence a magnitude of said flux of stimulated photonic radiation;

For each location within a first set of locations on the sample, accruing a spectrum using a first value of said beam parameter;

For each location within a second set of locations on the sample, accruing a spectrum using a second value of said beam parameter, different from said first value.

In research leading to the invention, the inventor arrived at the insight that, in many instances in which spectroscopy is performed, one is often (at least initially) more interested in qualitative analysis (i.e. whether a certain element is present at all) than in quantitative analysis (i.e. how much of that element is present); consequently, a certain distortion of spectral data—whereby the relative heights of peaks are manipulated—would, in many cases, yield acceptable results. In addition, the inventor realized that, while adjusting counting time might in principle provide a means of "augmenting" weaker peaks in a spectrum, it would not address the issue of pile-ups set forth above. In a novel approach to addressing these points, the inventor arrived at the idea of two-step (or multiple-step) spectroscopy, involving the accrual of spectra at different sample locations using different values of a suitable beam parameter of the input beam (such as beam current or beam energy, for example). Adjusting the selected beam parameter not only allows weak peak augmentation as referred to above, but it also allows adjustment of the intensity of the stimulated photonic flux produced from the sample, and thus of the occurrence of pile-ups in high-flux situations. Ideally, acquiring different spectra at different sample locations using different beam parameter values allows separate and yet concurrent optimization of data for both low- and high-brightness elements in the sample. For example:

Choosing a beam parameter value that will yield high photonic flux, one can examine the relatively weak spectral data from a low-brightness first element. A concurrently present high-brightness second element may cause significant occurrence of pile-ups, which will compromise the quality of the corresponding spectrum. In the prior-art, one would just have to live with this mismatch.

In the current invention, however, the previous spectral measurement is merely a first measurement. The current invention introduces a second measurement, in which the selected beam parameter is now adjusted so as to lower the observed photonic flux to a level that will mitigate the above-mentioned pile-up problem. A second spectrum is now measured, which will yield more reliable data for said second element.

Taken as a whole, a general sample of which a spectroscopic analysis has been made in accordance with the current invention may comprise a "mosaic" of different locations—some (ultimately) investigated using a first value of the beam current (lending itself to spectroscopy of high-brightness elements, for example), and others (ultimately) investigated using a second, different value of the beam parameter (lending itself to spectroscopy of low-brightness elements, for example). The word "ultimately" is used here because, at a given location, several different spectra may be accrued using different beam parameter values, and an optimal one of these (e.g. in terms of resolution/signal-to-noise ratio) may ultimately be graded as being the "best" specimen for a particular purpose (e.g. qualitative analysis); others of the accrued spectra may, of course, better lend themselves to other purposes (e.g. quantitative analysis). In this context, it should be noted that the first and second sets of locations stipulated here may overlap, or one may be a subset of the other, or they may be identical. Either subset (or both) may (or may not) correspond to the entire series of locations at which measurements are made.

What the invention is basically acknowledging is that, instead of trying to accrue spectra at all locations on a sample using a universal (blanket) value of said beam parameter, it may be better to adjust (tailor) the beam parameter as a function of location on the sample, and thus acquire a more optimal spectrum per location.

As set forth above, the flux of stimulated photonic radiation analyzed by the detector is generated by ejective interaction of the input beam of radiation with bound electrons in atoms of the sample. The input beam parameter adjusted in the present invention in order to control the magnitude of this flux does so by adjusting the reaction cross-section for said ejective interaction. This can, for example, be achieved in the following ways:

Adjusting the number of incoming particles in the input beam per unit of time, i.e. adjusting the beam intensity (which amounts to beam current in the case of a charged-particle beam). In the case of a Schottky emitter (or other source, such as a thermionic gun) used to produce electrons, beam current adjustment can, for example, be achieved by locating one or more condenser lenses and a diaphragm in the path of the electron beam, and using the condenser lens(es) to vary the diameter of the beam impinging upon the diaphragm; this correspondingly varies the current in the beam downstream of the diaphragm. On the other hand, in the case of an X-ray source that produces its output by decelerating a stream of electrons (producing Bremsstrahlung or synchrotron radiation, for example), the beam intensity can be adjusted by varying the current of said stream of electrons.

Adjusting the energy of individual particles in the incoming beam, which will influence the quantum efficiency of the ejective interaction. In the case of a charged-particle beam, this can be achieved by adjusting the magnitude of an electrical potential used to accelerate the beam, for example. Correspondingly, in the case of an X-ray source as alluded to above, the beam energy can be adjusted by varying the energy of said stream of electrons.

Adjusting the (effective) beam cross-section, e.g. using a diaphragm, or by varying the angle of incidence of the beam on the sample.

In the case of EDX/EDS, the inventor has found that beam current in particular lends itself to adjustment in the context of the present invention.

In one approach to the current invention, one might attempt to accrue (at least) two different spectra—at their respective beam parameter values—at a given location before moving on to the next location; such an approach can be referred to as entailing "on-the-fly" adjustment of the beam parameter. However, typically, adjustment of the beam parameter is a relatively slow process, so that on-the-fly adjustment thereof would tend to entail a significant throughput penalty. Consequently, an alternative embodiment of the method according to the present invention comprises the following steps:

Selecting said first value of the beam parameter;

In a first measurement run, maintaining said first value of the beam parameter whilst acquiring a spectrum for each location in said first set of locations;

Selecting said second value of the beam parameter;

In a second measurement run, maintaining said second value of the beam parameter whilst acquiring a spectrum for each location in said second set of locations.

This approach adjusts the beam parameter only once rather than on-the-fly. A particular embodiment of this approach will now be discussed.

As set forth above, prior-art spectroscopy approaches simply discard pile-up data when it occurs. The current inventor considers this to be wasteful and inefficient, and has devised an embodiment of the method according to the present invention in which pile-ups are more efficiently dealt with. Such an embodiment comprises the following steps:

During said first measurement run, generating an event signal if the detector encounters two successive photons that are separated by a temporal interval below a given acceptance value;

Generating a flag signal if, at a given location Lf, the number of generated event signals exceeds a particular threshold, and storing the location Lf in a memory;

In response to generation of a flag signal, choosing said second value of the beam parameter so as to reduce the magnitude of said flux of stimulated photonic radiation;

Choosing the second set of locations to include at least a subset of the locations Lf.

This embodiment exploits the intrinsic two-step approach of the current invention so as to flag and revisit significant pile-up locations on the sample. If pile-up data are blindly discarded—as in the prior art—then this results in a spectrum that is intrinsically of reduced quality (as set forth above). However, flagging locations on a sample at which significant pile-up behavior occurs will inform the spectroscope user that spectra from the locations in question are compromised, and will afford him the opportunity of re-accruing a spectrum at those locations using an adjusted beam parameter value that will lower stimulated photonic flux from the sample to a value that reduces pile-up events to less significant levels. In the context of this embodiment, the following should be noted:

Generation of an event signal as alluded to here is a statistical effect that can happen at any time, even for relatively low levels of stimulated photonic flux; this is the reason why a flag signal is only generated when the number of event signals at a particular location exceeds a pre-selected (discretionary) threshold, which defines what is considered to be statistically significant. Such a threshold value might be of the order of about 50, for example.

Said acceptance value (used in triggering event signals) will—for many commonly available detectors—also be adjustable. However, there is generally a trade-off between registration time and registration accuracy (energy resolution) in a detector as used in the current invention: choosing a shorter registration time (so as to decrease the chance of pile-ups) will produce an attendant decrease in the certainty with which the energy of a registered photon can be measured, and vice versa.

As regards said subset of locations Lf for which the second spectrum is accrued, this is discretionary, and will typically depend on the circumstances of a particular sample investigation, such as available time, importance of the sample, nature of the investigation, personal preference of the spectroscope user, etc. The subset may comprise all of the locations Lf, or just some of them. Second spectra may also be accrued for locations other than flag locations Lf, for example.

The skilled artisan will understand these points, and will be able to make appropriate choices in these matters as desired/required.

The skilled artisan will also appreciate that choice of the particular first and second values of the beam parameter employed in the method of the current invention is discretionary, and will generally depend on the particular circumstances of a given measurement/sample/user. For instance, taking beam current as a specific example of the employed beam parameter, if a first beam current value I1 is used to accrue a first spectrum at a given location and a pile-up flag is generated at this location, then the second beam current value I2 used to accrue a second spectrum at this location may be (for example):

Arbitrarily chosen, as part of an iterative "trial-and-error" approach. For example, one could choose I2=0.75 µl and, if pile-up behavior is still observed, resort to a still smaller value, such as I2=0.5 µl, etc.

Estimated using a model that encompasses the physics of generation of the stimulated photonic flux and of its detection, and calibrated/refined on the basis of previous measurements, for example.

Chosen based on previous experience with similar situations.

Similarly, if the employed first beam current value I1 does not cause generation of a pile-up flag at a particular location, then there is potentially room for one to choose a larger beam current value I2 in accruing a second spectrum at that location. The spectroscope used to perform the invention may be provided with a user interface on which the user can preselect values of the beam parameter to be used in first and second (and possibly further) measurement runs, and/or with a (semi-)autonomous processor that can itself decide on suitable beam parameter values.

As already set forth above, prior-art spectroscopic techniques tend to discard pile-up data when accruing spectra, since such data tend to be unreliable by their very nature. As previously remarked, this is wasteful and inefficient, and the present inventor sought a more practical alternative. To this end, in a further embodiment of the method according to the present invention:

If an event signal is generated at a location Le, the detector data associated with that event signal are stored in a buffer;

Data from this buffer are included in the accrued spectrum for location Le, but are labeled as being associated with an event signal.

In practice, such buffer data will manifest themselves as one or more extra peaks at dubious energy values (due to the fact that the detector's processing circuitry has misinterpreted two sequential photons of energies E1 and E2 as being a single photon of energy E1+E2). Though such false peaks cannot be "taken literally" in interpreting the resulting spectrum, they can nevertheless be a source of valuable information to an expert, who will generally be able to make an educated guess as to the separate energies E1, E2 underlying the false peaks; data divined in this way from the false peaks can then be used together will the real peaks in the spectrum to perform more accurate analyses of, for example, the quantity of an element generating the spectrum in question.

BRIEF DESCRIPTION OF THE DRAWINGS

The invention will now be elucidated in more detail on the basis of exemplary embodiments and the accompanying schematic drawings, in which.

In the Figures, where relevant, corresponding parts are indicated using corresponding reference symbols.

EMBODIMENT 1

Figure 1:
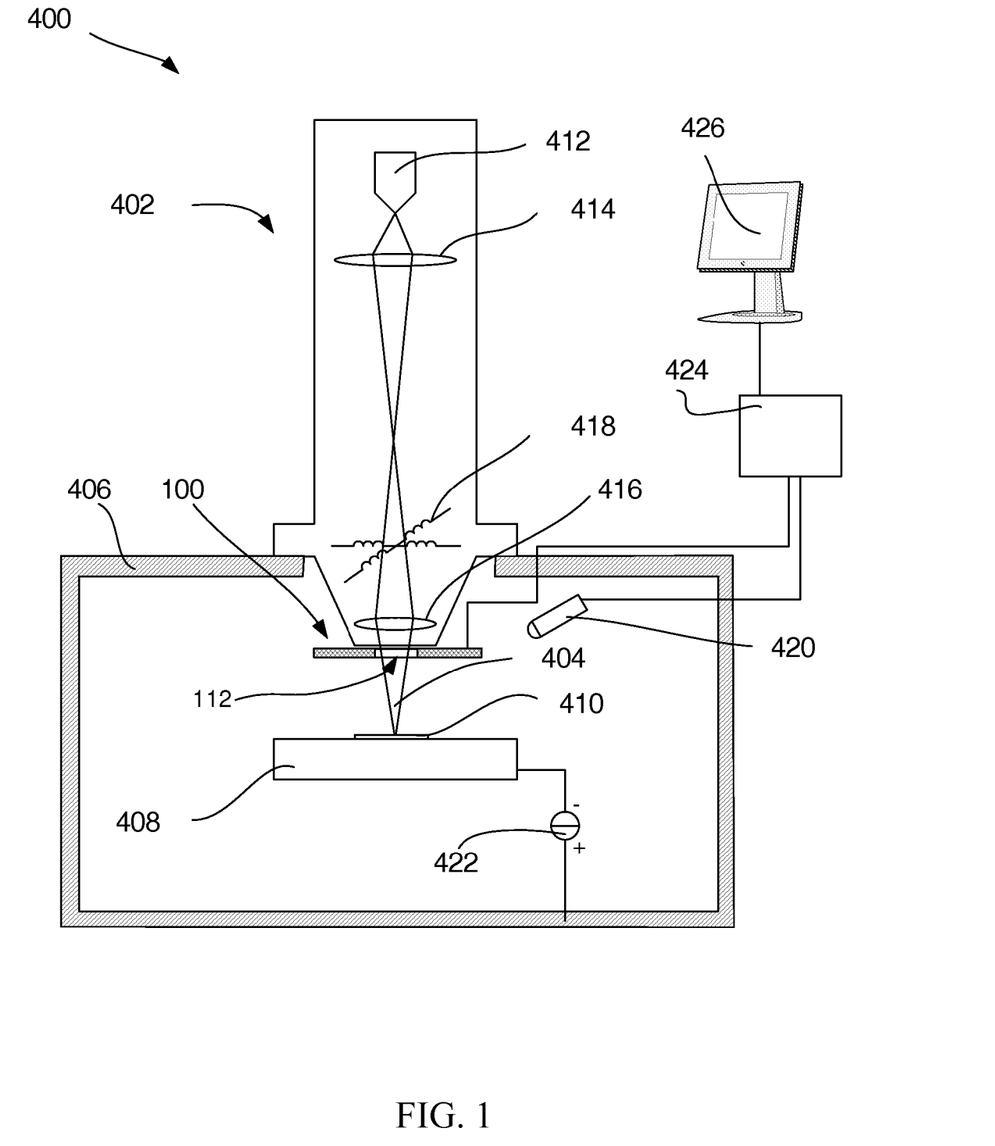
FIG. 1 renders a longitudinal cross-sectional view of aspects of a charged-particle microscope (in this case a SEM) with which the method according to the current invention can be performed.

FIG. 1 shows a charged-particle microscope 400, which, in this case, is a SEM. The microscope 400 comprises a particle-optical column 402, which produces a charged-particle beam 404 (in this case, an electron beam). The particle-optical column 402 is mounted on a vacuum chamber 406, which comprises a sample holder/stage 408 for holding a sample 410. The vacuum chamber 406 is evacuated using vacuum pumps (not depicted). With the aid of voltage source 422, the sample holder 408, or at least the sample 410, may be biased (floated) to an electrical potential with respect to ground.

The particle-optical column 402 comprises an electron source 412, a compound lens system 414, 416 to focus the electron beam 404 onto the sample 410, and a deflection unit 418. As regards detectors, the apparatus is equipped with:

A first detector 420, for detecting a flux of stimulated photonic radiation emanating from the sample 410 in response to irradiation by the beam 404. In the present example, the detector 420 is an X-ray detector such as an EDX/EDS detector.

A second detector 100, for detecting a different type of stimulated radiation emitted from the sample 410 in response to irradiation by the beam 404. In the present example, the detector 100 is a segmented electron detector, which can be used to detect backscatter electrons/secondary electrons, for example.

As here depicted, the apparatus uses both of these detector types; however, this is purely a design/implementation choice and, if desired, it's also possible to use just one of these detector types. The apparatus further comprises a computer processing apparatus (controller) 424 for controlling inter alia the deflection unit 418, lenses 414, and detectors 420, 100, and displaying information gathered from the detectors 420,100 on a display unit 426.

By scanning the beam 404 over the sample 410, stimulated radiation—comprising, for example, X-rays, infrared/visible/ultraviolet light, secondary electrons and backscatter (BS) electrons—emanates from the sample 410. As the emitted radiation is position-sensitive (due to said scanning motion), the information obtained from the detectors 420, 100, will also be position-dependent. The signals from the detectors 420,100 are processed by the processing apparatus 424, and displayed on display unit 426. Such processing may include operations such as combining, integrating, subtracting, false colouring, edge enhancing, and other processing known to the person skilled in the art. In addition, automated recognition processes, e.g. as used for particle analysis, may be included in such processing.

It should be noted that many refinements and alternatives of such a set-up will be known to the skilled artisan, including, but not limited to, the detection of (infrared/visible/ultraviolet) light emanating from the sample 410, the use of dual beams (for example an electron beam 404 for imaging and an ion beam for machining (or, in some cases, imaging) the sample 410), the use of a controlled environment at the sample 410 (for example, maintaining a pressure of several mbar—as used in a so-called Environmental SEM—or by admitting gasses, such as etching or precursor gasses), etc.

Figure 2:
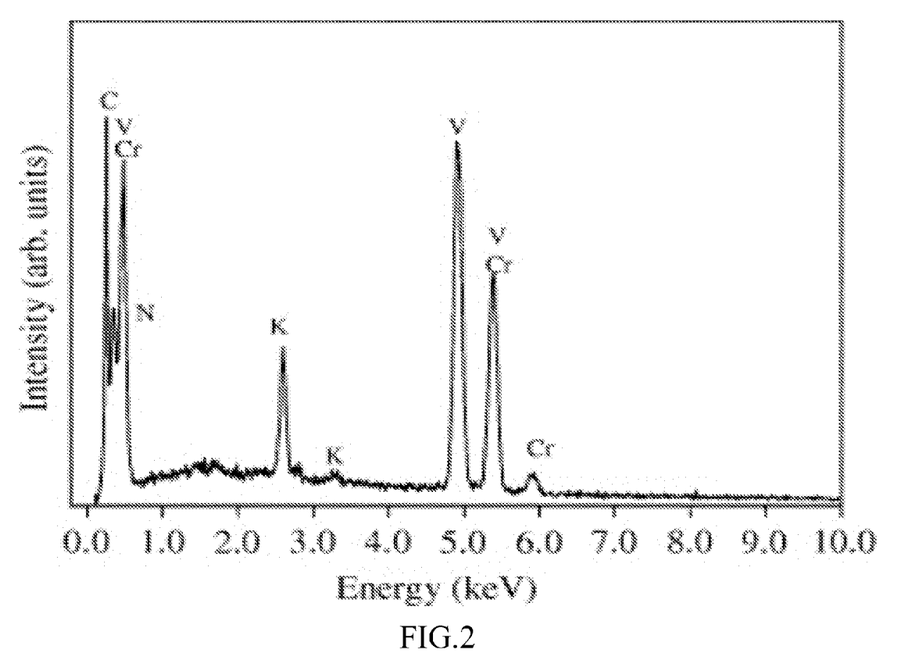
FIG. 2 shows an example of an EDX/EDS spectrum obtained for a particular metallurgical sample.

The depicted microscope 400 can used to accrue EDX/EDS spectra as follows:

The sample 410 is positioned with respect to the (non-depicted) optical axis of the beam 404 by moving the sample holder 408 and/or the beam 404. Such movement is effected so as to place a particular location of the sample 410 in the path of the beam 404;

When the beam 404 impinges on said location of the sample, it will generate (inter alia) a flux of X-rays (stimulated photonic radiation) as set forth above. This flux will comprise a stream of X-ray photons of (typically) various energies. Part of this flux impinges on a detection aperture of detector 420, which comprises a photoelectric converter. This converter generates a shower of electrons in response to registration of an X-ray photon, and this shower of electrons can then be processed by processing circuitry associated with the detector 420. Such circuitry may be within/on the detector and/or external thereto;

The detector 420 (together with its associated processing circuitry) is a so-called multi-channel detector, in that it is able to sort registered X-ray photons according to energy (channel), and count the number of registered events per channel. When such information is graphically rendered (for a given counting time/accumulation time), it yields a measured spectrum as illustrated in FIG. 2, for example (discussed in more detail later);

After a spectrum has been obtained in this way for said location, one can move on to a subsequent location on the sample 410, by causing appropriate relative motion of the sample holder 408 and the beam 404.

In the context of the present invention, not all such spectra are (ultimately) accrued using the same beam parameters of the beam 404. Instead, a beam parameter such as beam current is adjusted using certain components (e.g. condenser lenses) of the compound lens system 414, and one can accrue respective first and second spectra (at the same or different locations) using different values of this beam parameter. This approach can be of particular usefulness in situations in which data pile-up occurs during accumulation of the first spectrum; in such cases, the chosen beam parameter value is adjusted so as to (significantly) reduce stimulated photonic flux (of X-rays) from the sample 410, whence the occurrence of pile-ups during accrual of the second spectrum will be avoided, or at least reduced.

EMBODIMENT 2

FIG. 2 shows an EDX/EDS spectrum accrued from a metallurgical sample. The spectrum is a plot of measured Intensity along the ordinate (proportional to photon counts per channel) versus photon Energy in keV along the abscissa (determined by the channel into which a photon is sorted by the processing circuitry associated with the detector). The spectrum shows a number of distinct peaks that are superimposed upon a lower background.

The positions and relative heights of particular sets of these peaks are characteristic of the element generating them. For example, Vanadium (V) generates a trio of (distinguishable) peaks in the depicted spectrum, at energies of approx. 0.5, 4.9 and 5.4 keV. Chromium (Cr), on the other hand, is responsible for peaks at about 0.5, 5.4 and 5.95 keV (two of which apparently coincide with corresponding peaks of Vanadium at the employed energy resolution along the horizontal axis).

Figure 3A:
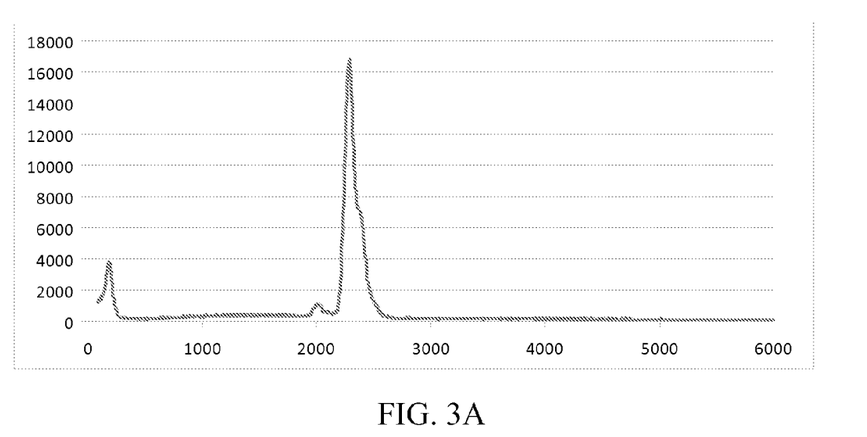
FIG. 3A-3C shows a collection of three EDX/EDS spectra for Molybdenum, accrued at different measurement settings (beam current, counting (accumulation) time, registration time).
Figure 3B:
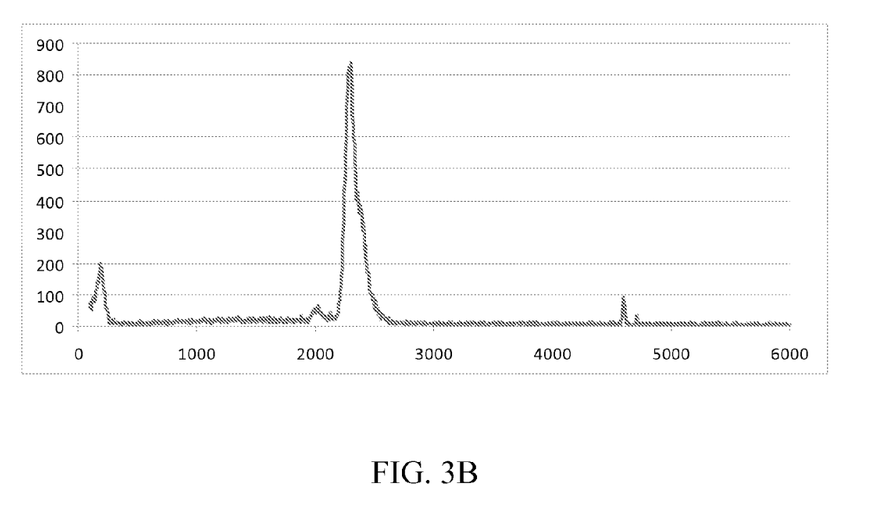
Figure 3C:
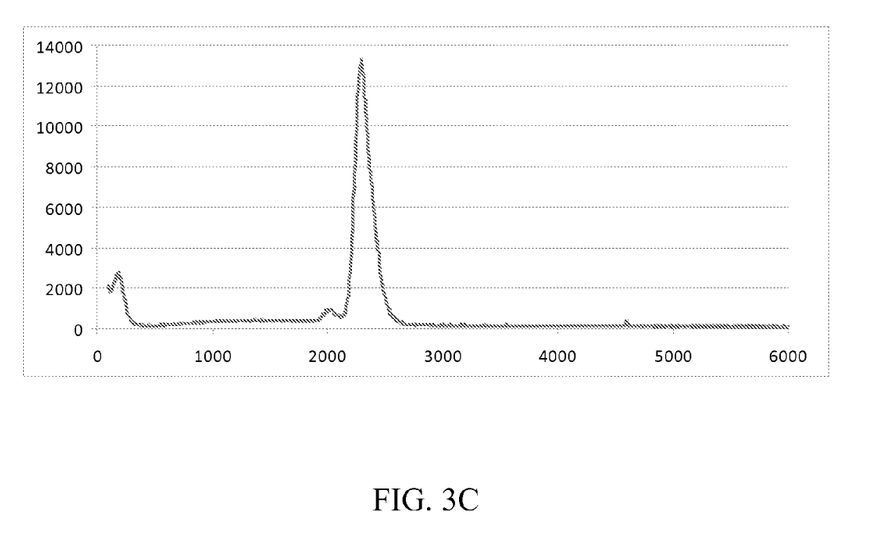

Moving on now to FIG. 3, this shows a collection of three EDX/EDS spectra for another sample, accrued at a location comprising a relatively high concentration of Molybdenum (Mo). The ordinate shows counts per channel, whereas the abscissa shows energy in eV. In the depicted energy range, Mo ideally exhibits two characteristic peaks—the so-called $L\alpha$ and $L\beta 1$ peaks. In more detail, the following is depicted:

FIG. 3A: This spectrum was accrued using a relatively low input beam current, relatively long counting (accumulation) time, and a relatively long registration time (low count rate). It is a relatively "ideal" spectrum in which the $L\alpha$ feature is clearly visible as a tall peak at about 2.29 keV, and the $L\beta 1$ feature manifests itself as a lower "shoulder" at about 2.37 keV. However, the spectrum's good detail and resolution come at the expense of throughput.

FIG. 3B: In an effort to increase throughput, this spectrum was accrued using a higher input beam current and a shorter counting (accumulation) time. Compared to FIG. 3A, there is a drastically lower number of counts, and the spectrum is correspondingly noisier. The $L\alpha$ and $L\beta 1$ features are still visible, but the increased noise levels make the $L\beta 1$ shoulder more difficult to discern. The reduced quality of the spectrum is due to a large incidence of pile-ups, most of which were discarded by the processing circuitry of the employed detector, but a small number of which "got through" (e.g. due to exactly simultaneous arrival of two photons), with small false peaks at about 4.6 and 4.7 keV as a consequence.

FIG. 3C: This spectrum was accrued using a shorter registration time, so as to decrease the incidence of pile-ups. As a result, counts are increased and noise is decreased. However, as already explained above, a shorter registration time brings an attendant decrease in energy resolution. Consequently, the $L\beta 1$ shoulder is now no longer (clearly) visible.

In this example, it is clear that, at least at the Mo-rich location in question, one can better use the spectrum of FIG. 3A than that of FIG. 3B or 3C. Consequently, at this Mo-rich location, a relatively low input beam current gives most satisfactory results. On the other hand, at another location in which a different element (concentration) has the overhand, a different beam current value might be recommendable. Thus arises the idea of a beam current (or other beam parameter) tailored to the particular sample location at which a spectrum is accrued.

I claim:

1. A method of examining a sample using a spectroscopic apparatus, comprising:
   mounting the sample on a sample holder;
   directing a focused input beam of radiation onto a location on the sample, thereby producing an interaction that causes a flux of stimulated photonic radiation to emanate from said location;
   examining said flux using a multi-channel photon-counting detector, thus accruing a measured spectrum for said location; and
   automatically repeating said directing and examining steps for a series of successive locations on the sample,
   choosing a beam parameter of the input beam that will influence a magnitude of said flux of stimulated photonic radiation;
   for each location within a first set of locations on the sample, accruing a spectrum using a first value of said beam parameter;
   for each location within a second set of locations on the sample, accruing a spectrum using a second value of said beam parameter, different from said first value.

2. The method of claim 1, comprising:
   selecting said first value of the beam parameter;
   in a first measurement run, maintaining said first value of the beam parameter whilst acquiring a spectrum for each location in said first set of locations;
   selecting said second value of the beam parameter; and
   in a second measurement run, maintaining said second value of the beam parameter whilst acquiring a spectrum for each location in said second set of locations.

3. The method of claim 2, comprising:
   during said first measurement run, generating an event signal if the detector encounters two successive photons that are separated by a temporal interval below a given acceptance value;
   generating a flag signal if, at a given location Lf, the number of generated event signals exceeds a particular threshold, and storing the location Lf in a memory;
   in response to generation of the flag signal, choosing said second value of the beam parameter so as to reduce the magnitude of said flux of stimulated photonic radiation; and
   choosing the second set of locations to include at least a subset of the locations Lf.

4. The method of claim 3, wherein:
   if an event signal is generated at a location Le, the detector data associated with that event signal are stored in a buffer; and
   data from this buffer are included in the accrued spectrum for location Le, but are labeled as being associated with an event signal.

5. The method of claim 1, in which:
   the input beam comprises radiation selected from the group comprising electrons, X-rays, gamma rays, protons, positrons or ions;
   the flux of stimulated photonic radiation comprises X-rays; and
   the beam parameter is selected from the group comprising current and intensity.

6. The method of claim 5, in which:
   the input beam comprises electrons; and
   the flux of stimulated photonic radiation is examined using Energy-Dispersive X-ray Spectroscopy.

7. A charged-particle microscope constructed and arranged to perform the method of claim 1.

8. A charged-particle microscope for examining a sample, comprising:
- a vacuum chamber including a sample holder for holding a sample;
- a particle optical column for producing a charged particle beam for irradiating the sample, thereby producing an interaction that causes a flux of stimulated photonic radiation to emanate from the sample;
- a first detector for detecting the flux of stimulated photonic radiation emanating from the sample;
- a second detector for detecting a different type of stimulated radiation emanating from the sample; and
- a computer processing controller including computer instructions for performing:
  - mounting the sample on a sample holder;
  - directing a focused input beam of radiation onto a location on the sample, thereby producing an interaction that causes a flux of stimulated photonic radiation to emanate from said location;
  - examining said flux using a multi-channel photon-counting detector, thus accruing a measured spectrum for said location; and
  - automatically repeating said directing and examining steps for a series of successive locations on the sample,
    - choosing a beam parameter of the input beam that will influence a magnitude of said flux of stimulated photonic radiation;
    - for each location within a first set of locations on the sample, accruing a spectrum using a first value of said beam parameter;
    - for each location within a second set of locations on the sample, accruing a spectrum using a second value of said beam parameter, different from said first value.

9. The charged-particle microscope of claim 8 in which the computer instructions comprise:
- selecting said first value of the beam parameter;
- in a first measurement run, maintaining said first value of the beam parameter whilst acquiring a spectrum for each location in said first set of locations;
- selecting said second value of the beam parameter; and
- in a second measurement run, maintaining said second value of the beam parameter whilst acquiring a spectrum for each location in said second set of locations.

10. The charged-particle microscope of claim 9 in which the computer instructions comprise:
- during said first measurement run, generating an event signal if the detector encounters two successive photons that are separated by a temporal interval below a given acceptance value;
- generating a flag signal if, at a given location Lf, the number of generated event signals exceeds a particular threshold, and storing the location Lf in a memory;
- in response to generation of the flag signal, choosing said second value of the beam parameter so as to reduce the magnitude of said flux of stimulated photonic radiation; and
- choosing the second set of locations to include at least a subset of the locations Lf.

11. The charged-particle microscope of claim 10 in which the computer instruction comprise:
- if an event signal is generated at a location Le, the detector data associated with that event signal are stored in a buffer; and
- data from this buffer are included in the accrued spectrum for location Le, but are labeled as being associated with an event signal.

12. The charged-particle microscope of claim 10 in which:
- the beam comprises radiation selected from the group comprising electrons, X-rays, gamma rays, protons, positrons or ions;
- the flux of stimulated photonic radiation comprises X-rays; and
- the beam parameter is selected from the group comprising current and intensity.

13. The charged-particle microscope of claim 12 in which:
- the input beam comprises electrons; and
- the flux of stimulated photonic radiation is examined using Energy-Dispersive X-ray Spectroscopy.

14. The charged-particle microscope of claim 8 in which the first detector comprises an x-ray detector.

15. The charged-particle microscope of claim 9 in which the x-ray detector is an EDX or EDS detector.

16. The charged-particle microscope of claim 8 in which the second detector comprises a segmented detector.

* * * * *